US007662777B2

(12) United States Patent
Iacobelli et al.

(10) Patent No.: US 7,662,777 B2
(45) Date of Patent: Feb. 16, 2010

(54) USE OF SULGLICOTIDE FOR THE TREATMENT OF MUCOSITIS

(75) Inventors: Massimo Iacobelli, Milan (IT); Laura Iris Ferro, Milan (IT)

(73) Assignee: Gentium SpA, Villa Guardia (IT)

( * ) Notice: Subject to any disclaimer, the term of this patent is extended or adjusted under 35 U.S.C. 154(b) by 303 days.

(21) Appl. No.: 11/569,095

(22) PCT Filed: May 12, 2005

(86) PCT No.: PCT/IT2005/000272

§ 371 (c)(1),
(2), (4) Date: Nov. 14, 2006

(87) PCT Pub. No.: WO2005/110458

PCT Pub. Date: Nov. 24, 2005

(65) Prior Publication Data

US 2008/0234180 A1 Sep. 25, 2008

(30) Foreign Application Priority Data

May 18, 2004 (IT) .................. MI2004A0989

(51) Int. Cl.
*A61K 38/00* (2006.01)
*A61K 9/14* (2006.01)
*C07K 1/00* (2006.01)
(52) U.S. Cl. .................. 514/2; 514/23; 424/485; 424/488; 424/499; 530/395
(58) Field of Classification Search ............ 514/2, 514/23; 424/485, 488, 499; 530/395
See application file for complete search history.

(56) References Cited

U.S. PATENT DOCUMENTS

| 5,085,867 | A | * | 2/1992 | Farolfi et al. ............ 424/485 |
| 5,496,828 | A | | 3/1996 | Cullinan et al. |
| 6,274,601 | B1 | * | 8/2001 | Cullinan ............ 514/324 |
| 2003/0064913 | A1 | | 4/2003 | Sonis |
| 2003/0236217 | A1 | | 12/2003 | Shalwitz et al. |

FOREIGN PATENT DOCUMENTS

EP 0 274 745 A 7/1988
WO WO 92/18153 A 10/1992

OTHER PUBLICATIONS

Piotrowski et al. Enhancement in Gastric Mucosal EGF and PDGF Receptors Expression with Ulcer Healing by Sulglycotide, 1995, Genral Pharmacology, vol. 26, No. 4, pp. 749-753.*
Slomiany et al. Suppression of gastric mucosal inflammatory responses to Helicobacter pylori lipopolysaccharide by sulglycotide, 1999, General Pharmacology, vol. 32, pp. 251-257.*
Slomiany et al. Omerazole Failsto Suppress Up-Regulation of Gastric Mucosal Endothelin-Converting Enzyme-1 by Helicobacter Pylori Lipopolysaccharide, 2000, Journal of Physiology and Pharmacology, vol. 51, No. 3, pp. 421-431.*
Database Biosis 'Online! Biosciences Information Service, 1995, "Enhancement in gastric mucosal EGF and PDGF receptor expression with ulcer healing by sulglycotide" Abstract.
Demarosi, F. et al, Prevention and Treatment of Chemo- and Radiotherapy-Induced Oral Mucositis, Minerva Stomatologica, 2002, pp. 173-186, vol. 51.
Pico, J., et al, Mucositis: Its Occurrence, Consequences, and Treatment in the Oncology Setting, The Oncologist, 1998, pp. 446-451, vol. 3.
Peterson, Douglas E., Research advances in oral mucositis, Current Opinion in Oncology, 1999, pp. 261-266, vol. 11.
Plevova, P., Prevention and treatment of chemotherapy- and radiotherapy- induced oral mucositis: a review, Oral Oncology, 1999, pp. 453-470, vol. 35.
Porro, G. B., et al, Sulglycotide in the Prevention of Nonsteroidal Anti-inflammatory Drug-Induced Gastroduodenal Mucosal Injury, Sulglycotide in Preventing Mucosal Injury, 1993, pp. 875-878, vol. 28 (10).
Slomiany, B.L., et al, Endothelin-1, Interleukin-4 and Nitric Oxide Synthase Modulators of Gastric Mucosal Injury by Indomethacin: Effect of Antiulcer Agents, Journal of Physiology and Pharmacology, 1992, pp. 197-210, vol. 50 (2).
Sonis, S.T., Mucositis as a biological process: a new hypothesis for the development of chemotherapy-induced stomatotoxicity, Oral Oncology, 1998, pp. 39-43, vol. 34.

* cited by examiner

*Primary Examiner*—Jon P Weber
*Assistant Examiner*—Abdel A Mohamed
(74) *Attorney, Agent, or Firm*—Fredrikson & Byron, P.A.

(57) ABSTRACT

A method for the treatment and/or prevention of mucositis due to an antitumour treatment which comprises the administration of a composition containing suiglicotide to a patient in needs of said antitumour treatment.

6 Claims, 3 Drawing Sheets

FIG. A

FIG. B

FIG. C

USE OF SULGLICOTIDE FOR THE TREATMENT OF MUCOSITIS

RELATED APPLICATIONS

This application claims priority to International Application No. PCT/IT2005/000272, filed 12 May 2005 and to Italian Application No. MI2004A000989 filed 18 May 2004, the teachings of which are incorporated herein by reference.

BACKGROUND OF THE INVENTION

Mucositis is a common inflammatory condition affecting the mucous membranes, in particular following chemotherapy or radiotherapy in patients suffering from tumours.

These types of therapy, in addition to acting on neoplastic cells, in fact also act upon the cells of healthy tissue, especially those which replicate rapidly.

As a result, the oral cavity is one of the areas which is highly affected by the complications arising from such treatment; indeed, virtually all patients treated for tumours of the head and neck, and around 40% of those subjected to radiochemotherapy for tumours in other locations (leukaemias or lymphomas) develop complications affecting the oral cavity (Minerva Stomatol. 2002:51:173-86).

In general, the term "mucositis" is understood to mean a clinical picture characterised by the presence of reduced epithelial thickness, intense erythema and ulcers, associated with a painful symptom complex and the possible occurrence of infection and haemorrhage (Oncologist 1998:3:446-52; Oncologist 1999:11:261-6).

The biological mechanism underlying the development of mucositis, in particular oral mucositis, is subdivided into four phases: an initial inflammatory/vascular phase during which, following radio- or chemotherapy, the epithelial tissues release a large quantity of cytokines such as, for example, interleukin 1 or TNF-α, which cause the first localised tissue damage; a second epithelial phase which affects the division of the epithelial basal cells, resulting in reduced renewal of said cells, atrophy and ulceration of the tissue; a third ulcerative/bacterial phase, which is when the symptoms are at their most intense, with bacterial colonisation of the lesion. This third phase also coincides with severe neutropaenia of the patient; the fourth and final characteristic phase of mucositis is considered to be the healing phase with recovery of proliferation and differentiation of epithelial cells, a progressive increase in white cells and normalisation of the local bacterial flora.

At present, both preventive and curative treatment is provided for mucositis. In the first case, agents are used which are capable of reducing mucous absorption of the chemotherapy drugs (for example cryotherapy, allopurinol or pilocarpine etc.), agents which reduce the changes in epithelial proliferation (for example beta-carotene, glutamine or silver nitrate etc.) or antiinflammatory and antimicrobial agents (for example, mesalazine and/or chlorhexidine).

In particular, with regard to mucositis of the oral cavity, cryotherapy is today the most widely recognised preventive treatment; this method is based on the administration of ice cubes to be kept in the mouth for a period of 30 minutes with the aim of bringing about vasoconstriction of the oral mucosa in order to reduce the temperature-dependent toxicity of some chemotherapeutics. Unfortunately, cryotherapy has proved to exhibit substantial preventive effectiveness only in patients treated with chemotherapeutics which can be administered as a bolus (fluorouracils) but has proved ineffective for continuously perfused chemotherapeutics because the drug is permanently present in the circulating blood and local vasoconstriction locale is of no benefit (Oral Oncology 1999; 35:453-70).

In the second case, use is made of agents which protect the mucosa (for example, sodium bicarbonate), anaesthetic or analgesic agents (for example, lidocaine, morphine and the derivatives thereof etc.), agents which accelerate the healing process (for example, vitamin E, tretinoin, laser therapy etc.) or special diets and/or specific oral hygiene regimens.

Other methods for treating mucositis are described in US patent applications US2003/0064913 and US2003/0236217, which are incorporated herein by reference.

However, none of these preventive strategies or therapeutic approaches has proved entirely effective in the prevention or treatment of mucositis, in particular due to chemotherapy and/or radiotherapy, which remains a cause of suffering in patients suffering from tumours, such as in mucositis of the oral cavity in patients with head and/or neck tumours.

Sulglicotide is a sulfuric polyester of a glycopeptide obtained by extraction from pig duodenum. Sulglicotide is obtained by enzymatic proteolysis, repeated purification and subsequent sulfation steps; the final product is identified by electrophoresis on cellulose acetate.

Sulglicotide is a gastroprotective and antiulcer drug; it is not absorbed intestinally and is known to produce its effects only within the gastric lumen.

Indeed, sulglicotide is usually administered as a gastroprotective to individuals whose stomach wall has been attacked by drugs such as, for example, aspirin and taurocholic acid or by generic nonsteroidal antiinflammatory drugs. Clinical studies have demonstrated the effectiveness of administering sulglicotide to patients suffering from rheumatoid arthritis and receiving treatment with indomethacin and diclofenac, so preventing the occurrence of gastric or duodenal ulceration associated with the use of such nonsteroidal antiinflammatories (Scand. J. Gastroenterol. 1993; October; 28(10):875-8).

The mechanism of action, apart from being linked to pepsin inactivation, is due to the stimulation of the secretion of mucous and bicarbonate by the cells of the gastric mucosa.

In particular, sulglicotide is known to be the drug of choice for the treatment of gastric conditions associated with *Helicobacter pylori* inflammation.

*Helicobacter pylori* is a spiral-shaped, gram-negative bacterium which, thanks to its various characteristics, survives in the acidic environment of the gastric mucosa and proliferates under the mucous which coats the internal wall of the stomach, adhering to the cells of the mucosa itself. It is the cause of duodenal ulcers as well as being one of the main causes of chronic gastritis. Current treatments are based on antibiotics and, in the ever more frequent event of antibiotic-resistant strains and relapse, on specific antiulcer drugs.

Indeed, both in animal models and in various clinical studies, the administration of sulglicotide has brought about a considerable antiulcer action in the stomach, with a substantial improvement in the inflammation due to *H. pylori* (J. Physiol. Pharmacol. 1999 June; 50(2):197-210). Sulglicotide principally acts by inhibiting the effect of the LPS (lipopolysaccharide) produced by the bacterium which prevents somatostatin-receptor binding, causing overproduction of gastrin and acidic secretions which are responsible for the subsequent formation of the ulcer.

SUMMARY OF THE INVENTION

It has now surprisingly been found that using suiglicotide in the treatment of mucositis brings about a considerable improvement with regard to the inflammatory symptom complex and to mucosal damage, with functioning of epithelial cells being significantly restored.

In particular, sulglicotide exhibits its effectiveness in the treatment of mucositis of the oral cavity. More particularly, sulglicotide is active in the treatment of mucositis due to chemotherapy and/or radiotherapy.

Sulglicotide, by increasing levels of both type $PGE_2$ and type $PGI_2$ prostaglandins, brings about increased secretion of mucous and normalised renewal of the epithelial cells of the mucosa. Furthermore, sulglicotide is capable of increasing the secretion of EGF (Epidermal Growth Factor) and so ensuring both the onset of much less severe conditions of the mucosa, and the acceleration of the healing process of such conditions.

The increase in the quantity of EGF, or of the receptor thereof, in fact brings about increased proliferation of the epithelial cells with the formation of a superstratum of said cells and consequent thickening of the mucosa, in particular the oral and/or gastrointestinal mucosa, which is so able to act as a barrier to attack from cytotoxic agents (for example radiation) and significantly reduce any damage.

Growth factors, EGF in particular, are factors which essentially determine the sensitivity of the epithelial cells towards cytotoxic agents.

Thus, the use of sulglicotide in mucositis, in particular mucositis of the oral cavity and used before and/or during chemotherapy and/or radiotherapy in patients suffering from tumours, such as tumours of the head and neck (for example laryngeal, pharyngeal or oesophageal carcinoma), results in a reduction in the damage to the mucosa and lower toxicity of said antitumour treatments, with subsequent resolution of the mucositis associated therewith.

Consequently, according to the present invention, sulglicotide is active in the prevention and treatment of mucositis, in particular oral mucositis due to antitumour treatments such as chemotherapy and/or radiotherapy.

BRIEF DESCRIPTION OF THE DRAWING

FIG. A is an illustration of the morphology of a normal intestinal crypt.

FIG. B is an illustration of the morphology of an intestinal crypt after irradiation with centers of regeneration.

FIG. C is an illustration of the morphology of an intestinal crypt containing fewer than 10 cells.

DETAILED DESCRIPTION OF ONE EMBODIMENT

Animal testing was carried out with the aim of assessing the efficacy of suiglicotide in protecting the clonogenic cells of the intestinal mucosa from radiation-induced damage. Protection of the clonogenic cells ensures the survival of the intestinal crypt which promotes the restoration of the normal epithelium.

The animals treated in the present test are free from *H. pylori*, or their gastrointestinal mucosa does not exhibit the characteristic signs of inflammation brought about by this bacterium.

In the present test, the inflammatory damage was caused by a 13 Gy X-ray dose. 60 male BDF1 mice, divided into 10 groups each of 6 animals, were treated.

Sulglicotide was administered daily as a preventive measure to 4 groups (plus one control/saline solution group) via a gastric tube and at various doses, namely respectively 12 mg/kg, 50 mg/kg, 200 mg/kg and 800 mg/kg three days before irradiation with a final dose 30 minutes before irradiation.

The other 4 groups (plus one control/saline solution group) received sulglicotide as a treatment, again via a gastric tube and at various doses, namely respectively 12.5 mg/kg, 50 mg/kg, 200 mg/kg and 800 mg/kg immediately after irradiation and thereafter daily for 3 days before sacrifice on the 4th day.

All the animals survived the treatment and no adverse affects were observed. The animals were collected 4 days after irradiation and sacrificed. 10 intestinal circumferences were measured for each animal (60 per group) and the number of surviving crypts and their width was assessed, a mean being calculated for each group. Only intact circumferences and crypts containing 10 or more clonogenic cells were included.

The data obtained are summarised in Table 1 below. The attached Figures show the normal intestinal morphology (Fig. A) or after irradiation with centres of regeneration in which surviving crypts can be seen with only one or more clonogenic cells and the remaining mesenchyme completely lacking (Fig. B). These individuals develop diarrhoea and die from mucositis. Figure C shows an intestinal morphology with phantom crypts or crypts containing fewer than 10 cells.

TABLE 1

| Treatment | Mouse no. | No. crypts/ circumference | Crypt length/μm | Corrected crypts/ circumference |
|---|---|---|---|---|
| 12.5 mg/kg sulglicotide pretreatment | 1 | 6.8 | 46.61 | 4.6 |
| | 2 | 5.4 | 52.09 | 3.3 |
| | 3 | 14.5 | 50.40 | 9.1 |
| | 4 | 7.8 | 47.22 | 5.2 |
| | 5 | 6.7 | 45.33 | 4.7 |
| | 6 | 5.8 | 52.08 | 3.5 |
| | Mean | 7.8 | 48.95 | 5.1 |
| 50 mg/kg sulglicotide pretreatment | 1 | 1.6 | 45.17 | 1.1 |
| | 2 | 2.5 | 54.43 | 1.5 |
| | 3 | 2.5 | 40.12 | 2.0 |
| | 4 | 6.9 | 48.67 | 4.5 |
| | 5 | 12 | 45.76 | 8.3 |
| | 6 | 5.6 | 51.80 | 3.4 |
| | Mean | 5.2 | 47.68 | 3.5 |
| 200 mg/kg sulglicotide pretreatment | 1 | 11.3 | 40.44 | 8.9 |
| | 2 | 10.5 | 47.86 | 7.0 |
| | 3 | 11.0 | 50.46 | 6.9 |
| | 4 | 7.0 | 49.07 | 4.5 |
| | 5 | 9.0 | 49.44 | 5.8 |
| | 6 | 9.8 | 46.99 | 6.6 |
| | Mean | 9.8 | 47.38 | 6.6 |
| 800 mg/kg sulglicotide pretreatment | 1 | 8.6 | 44.77 | 6.1 |
| | 2 | 7.4 | 47.92 | 4.9 |
| | 3 | 7.3 | 51.44 | 4.5 |
| | 4 | 10.2 | 49.36 | 6.6 |
| | 5 | 8.2 | 51.09 | 5.1 |
| | 6 | 3.1 | 42.28 | 2.3 |
| | Mean | 7.5 | 47.81 | 4.9 |
| Control saline pretreatment | 1 | 10.3 | 51.12 | 6.4 |
| | 2 | 8.3 | 46.17 | 5.7 |
| | 3 | 2.8 | 51.84 | 1.7 |
| | 4 | 4.2 | 52.28 | 2.6 |
| | 5 | 4.5 | 45.01 | 3.2 |
| | 6 | 13.1 | 43.01 | 9.7 |
| | Mean | 7.2 | 48.24 | 4.9 |
| 12.5 mg/kg sulglicotide posttreatment | 1 | 8.1 | 43.35 | 5.9 |
| | 2 | 1.8 | 49.16 | 1.2 |
| | 3 | 5.5 | 44.09 | 4.0 |
| | 4 | 2.9 | 41.04 | 2.2 |
| | 5 | 7.7 | 51.00 | 4.8 |
| | 6 | 1.5 | 46.65 | 1.0 |
| | Mean | 4.6 | 45.88 | 3.2 |

TABLE 1-continued

| Treatment | Mouse no. | No. crypts/ circumference | Crypt length/μm | Corrected crypts/ circumference |
|---|---|---|---|---|
| 50 mg/kg sulglicotide posttreatment | 1 | 9.8 | 49.70 | 6.3 |
| | 2 | 7.6 | 49.32 | 4.9 |
| | 3 | 4.4 | 53.89 | 2.6 |
| | 4 | 3.7 | 48.85 | 2.4 |
| | 5 | 5.8 | 45.86 | 4.0 |
| | 6 | 13.8 | 48.53 | 9.0 |
| | Mean | 7.5 | 49.36 | 4.9 |
| 200 mg/kg sulglicotide posttreatment | 1 | 10.4 | 46.25 | 7.1 |
| | 2 | 7.3 | 46.29 | 5.0 |
| | 3 | 8.1 | 52.88 | 4.9 |
| | 4 | 5.9 | 45.86 | 4.1 |
| | 5 | 5.7 | 58.58 | 3.1 |
| | 6 | 4.0 | 51.00 | 2.5 |
| | Mean | 6.9 | 50.14 | 4.5 |
| 800 mg/kg sulglicotide posttreatment | 1 | 16.7 | 42.06 | 12.6 |
| | 2 | 12.2 | 48.03 | 8.1 |
| | 3 | 6.6 | 42.40 | 4.9 |
| | 4 | 5.6 | 43.95 | 4.0 |
| | 5 | 3.8 | 45.00 | 2.7 |
| | 6 | 8.3 | 42.33 | 6.2 |
| | Mean | 8.9 | 43.96 | 6.4 |
| Control saline posttreatment | 1 | 8.8 | 53.52 | 5.2 |
| | 2 | 10.2 | 49.95 | 6.5 |
| | 3 | 3.4 | 53.08 | 2.0 |
| | 4 | 11.1 | 47.30 | 7.5 |
| | 5 | 4.6 | 49.92 | 2.9 |
| | 6 | 5.3 | 49.58 | 3.4 |
| | Mean | 7.2 | 50.56 | 4.6 |
| Control | 1 | 101 | 34.99 | |
| | 2 | 97.7 | 32.15 | |
| | 3 | 91.4 | 31.73 | |
| | 4 | 93.4 | 28.89 | |
| | 5 | 96.3 | 31.78 | |
| | 6 | 95.4 | 30.9 | |
| | Mean | 95.7 | 31.74 | |

Results:

The data collected emphasise the efficacy of sulglicotide on irradiation damage and the association between efficacy and the different dose administered. At the lowest doses (12.5 mg/kg and 50 mg/kg), sulglicotide does not exhibit any preventive effect on the damage to clonogenic cells and the intestinal crypts; evidence of increased survival of the crypts and thus of protection from irradiation damage is found at a dose of 200 mg/kg (35%). A dose of greater than 200 mg/kg also exhibits no protective efficacy. However, while it is effective in preventive terms, the dose of 200 mg/kg exhibits no activity in the post-irradiation treatment groups.

In these cases, only the higher dose of 800 mg/kg has any significant therapeutic effect on the damage caused by the X-rays.

In conclusion, sulglicotide, administered to mice free from *Helicobacter pylori* via a gastric tube at various doses, proves to be effective in the prevention or treatment of radiation damage.

The invention claimed is:

1. A method for the treatment and/or reduction of oral mucositis due to an antitumor treatment which comprises the administration of a composition consisting essentially of sulglicotide to a patient receiving said antitumour treatment.

2. A method according to claim 1 in which the antitumour treatment is chemotherapy and/or radiotherapy.

3. A method according to claim 1 in which the sulglicotide is administered in a quantity of from 12.5 mg/kg to 800 mg/kg.

4. A method according to claim 1 in which said compositions are topical dosage forms.

5. A method according to claim 1 in which said pharmaceutical compositions are oral dosage forms.

6. A method according to claim 1 in which said compositions are parenteral dosage forms.

* * * * *

UNITED STATES PATENT AND TRADEMARK OFFICE
CERTIFICATE OF CORRECTION

PATENT NO. : 7,662,777 B2
APPLICATION NO. : 11/569095
DATED : February 16, 2010
INVENTOR(S) : Iacobelli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this

Twenty-eighth Day of December, 2010

David J. Kappos
*Director of the United States Patent and Trademark Office*